US007653176B2

(12) United States Patent
Smith et al.

(10) Patent No.: US 7,653,176 B2
(45) Date of Patent: Jan. 26, 2010

(54) INSPECTION SYSTEM WITH MATERIAL IDENTIFICATION

(75) Inventors: Richard C. Smith, Pinellas Park, FL (US); Robert W. Madden, Seminole, FL (US); James M. Connelly, St. Petersburg, FL (US)

(73) Assignee: L-3 Communications Security and Detection Systems Inc., Woburn, MA (US)

( * ) Notice: Subject to any disclaimer, the term of this patent is extended or adjusted under 35 U.S.C. 154(b) by 218 days.

(21) Appl. No.: 11/453,545

(22) Filed: Jun. 14, 2006

(65) Prior Publication Data

US 2006/0291622 A1 Dec. 28, 2006

Related U.S. Application Data

(60) Provisional application No. 60/690,281, filed on Jun. 14, 2005, provisional application No. 60/690,440, filed on Jun. 14, 2005.

(51) Int. Cl.
*H01L 27/146* (2006.01)
*G21K 5/10* (2006.01)

(52) U.S. Cl. .............. 378/69; 250/370.08; 250/306; 250/307; 250/370.09; 378/11; 378/29; 378/55; 378/57; 378/62

(58) Field of Classification Search .......... 250/306, 250/307, 309, 492.1, 442.11, 370.09, 370.08, 250/370.1; 378/4, 8, 10, 11, 20, 22, 29, 30, 378/46, 53–55, 57, 62, 69, 82, 83, 87, 89, 378/90, 101, 102, 140, 145–147, 149–151
See application file for complete search history.

(56) References Cited

U.S. PATENT DOCUMENTS

| | | | | | |
|---|---|---|---|---|---|
| 3,919,417 | A | * | 11/1975 | Bennett et al. | 514/63 |
| 3,924,064 | A | * | 12/1975 | Nomura et al. | 378/57 |
| 4,599,740 | A | * | 7/1986 | Cable | 378/57 |
| 4,803,639 | A | * | 2/1989 | Steele et al. | 702/40 |
| 5,367,552 | A | | 11/1994 | Peschmann | |
| 5,600,303 | A | * | 2/1997 | Husseiny et al. | 340/568.1 |
| 5,760,901 | A | * | 6/1998 | Hill | 356/450 |
| 6,118,850 | A | | 9/2000 | Mayo et al. | |
| 6,324,249 | B1 | * | 11/2001 | Fazzio | 378/22 |
| 6,583,420 | B1 | * | 6/2003 | Nelson et al. | 250/397 |
| 6,856,667 | B2 | * | 2/2005 | Ellengogen | 378/57 |
| 6,937,692 | B2 | * | 8/2005 | Johnson et al. | 378/57 |
| 7,050,535 | B2 | * | 5/2006 | Georgeson et al. | 378/57 |
| 7,356,116 | B2 | * | 4/2008 | Anwar et al. | 378/57 |
| 7,397,891 | B2 | * | 7/2008 | Johnson et al. | 378/57 |

(Continued)

*Primary Examiner*—Bernard E Souw
(74) *Attorney, Agent, or Firm*—Wolf, Greenfield & Sacks, P.C.

(57) ABSTRACT

An angular analysis system that can be controlled to receive radiation at a defined angle from a defined focus region. The angular analysis system is used for level 2 inspection in an explosive detection system. Level 2 inspection is provided by a three-dimensional inspection system that identifies suspicious regions of items under inspection. The angular analysis system is focused to gather radiation scattered at defined angles from the suspicious regions. Focusing may be achieved in multiple dimensions by movement of source and detector assemblies in a plane parallel to a plane holding the item under inspection. Focusing is achieved by independent motion of the source and detector assemblies. This focusing arrangement provides a compact device, providing simple, low cost and accurate operation.

23 Claims, 8 Drawing Sheets

U.S. PATENT DOCUMENTS

| | | | |
|---|---|---|---|
| 7,436,991 B2* | 10/2008 | Greenbaum et al. | 382/128 |
| 7,519,152 B2* | 4/2009 | Smith et al. | 378/69 |
| 2002/0172324 A1* | 11/2002 | Ellengogen | 378/57 |
| 2002/0176534 A1 | 11/2002 | Meder | |
| 2003/0215054 A1* | 11/2003 | Fenkart et al. | 378/57 |
| 2004/0120456 A1* | 6/2004 | Ellenbogen | 378/57 |
| 2004/0247075 A1* | 12/2004 | Johnson et al. | 378/57 |
| 2005/0008120 A1* | 1/2005 | Ellenbogen | 378/57 |
| 2005/0047637 A1* | 3/2005 | Greenbaum et al. | 382/132 |
| 2005/0104603 A1* | 5/2005 | Peschmann et al. | 324/637 |
| 2005/0281383 A1* | 12/2005 | Harding et al. | 378/149 |
| 2006/0049351 A1* | 3/2006 | Bushberg et al. | 250/336.1 |
| 2006/0056585 A1* | 3/2006 | Georgeson et al. | 378/57 |
| 2006/0291622 A1* | 12/2006 | Smith et al. | 378/69 |
| 2006/0291623 A1* | 12/2006 | Smith et al. | 378/69 |
| 2007/0165777 A1* | 7/2007 | Anwar et al. | 378/57 |
| 2007/0223656 A1* | 9/2007 | Gusterson | 378/146 |

* cited by examiner

INSPECTION SYSTEM WITH MATERIAL IDENTIFICATION

RELATED APPLICATIONS

This application claims priority under 35 U.S.C. § 119(e) to U.S. Provisional Application Ser. No. 60/690,281, entitled "MOVING SOURCE AND DETECTOR COLLIMATION AND TARGETING INSPECTION SYSTEM FOR MATERIAL IDENTIFICATION BY ENERGY-DISPERSIVE COHERENT X-RAY SCATTERING OR FLUORESCENT EMMISSIONS," filed on Jun. 14, 2005, which is herein incorporated by reference in its entirety.

This application claims priority under 35 U.S.C. § 119(e) to U.S. Provisional Application Ser. No. 60/690,440, entitled "COHERENT X-RAY SCATTERING SYSTEM WITH EXTERNAL POWER SUPPLY," filed on Jun. 14, 2005, which is herein incorporated by reference in its entirety.

BACKGROUND OF INVENTION

1. Field of Invention

This application relates generally to material identification and more specifically to inspection systems that perform material identification.

2. Discussion of Related Art

Inspection systems are widely used to obtain information on objects that cannot be readily seen in an external examination of items under inspection. Inspection systems are used as part of security systems, such as explosive detection systems, used at airports or other settings to preclude people from smuggling explosives into a secure area by concealing them in packages. Though, inspection systems may also be used during mail processing to obtain information on objects in packages, during mail processing on bones or other structures inside a human body during medical testing, on objects in food products as part of health inspections, on minerals in ore as part of a mining operation and in many other settings.

Frequently, inspection systems use penetrating radiation, such as x-rays. The inspection system captures the radiation after it has interacted with an item under inspection. Analysis of the radiation reveals properties of objects inside the item under inspection. Based on this analysis, a security system can "clear" an item by determining that it contains only innocuous objects or can "alarm" an object by determining that it likely contains one or more objects that pose a threat. Other inspection systems may cause other actions based on the properties of the objects identified in the inspection.

In capturing radiation, some inspection systems discriminate between radiation emanating from an object at different angles. Angular discrimination may be used in conjunction with a focusing system that passes only radiation from a specific region on which data is to be collected. In some instances, controlling the measurement angle reveals information useful for analyzing an object. For example, the angle at which radiation scatters from an object is an indication of the type of material that makes up the object. As one example, x-ray diffraction analysis may be used to analyze the spectrum of radiation scattered from a region of an item under inspection to determine whether that region contains innocuous material or a threat material.

SUMMARY OF INVENTION

In one aspect, the invention relates to an inspection system that has a conveyor adapted to move items in a first direction. The system has a source assembly with an x-ray source adapted to irradiate an item on the conveyor and a source collimator positioned between the x-ray source and the conveyor. A first positioning mechanism is adapted and arranged to move the source assembly in a second direction, transverse to the first direction. The system also has a detector assembly with a detector and a detector collimator positioned between the detector and the conveyor. A second positioning mechanism is adapted and arranged to move the detector assembly in the second direction. The second positioning mechanism can be controlled in at least one direction independently of the first positioning mechanism.

In another aspect, the invention relates to a method of operating an inspection system having a source, a detector and an inspection region adapted and arranged to position an item under inspection in a plane. According to the method, the source and the detector move parallel to the plane to create a focus region in an item under inspection. The source radiates the focus region and the detector measures radiation emanating at an angle from the focus region. The measured radiation is then analyzed.

In another aspect, the invention relates to a method of operating an inspection system. The method includes moving an item through an inspection area; and gathering data on a focus region of the item using a source and a detector while moving the source and the detector synchronously with the item.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
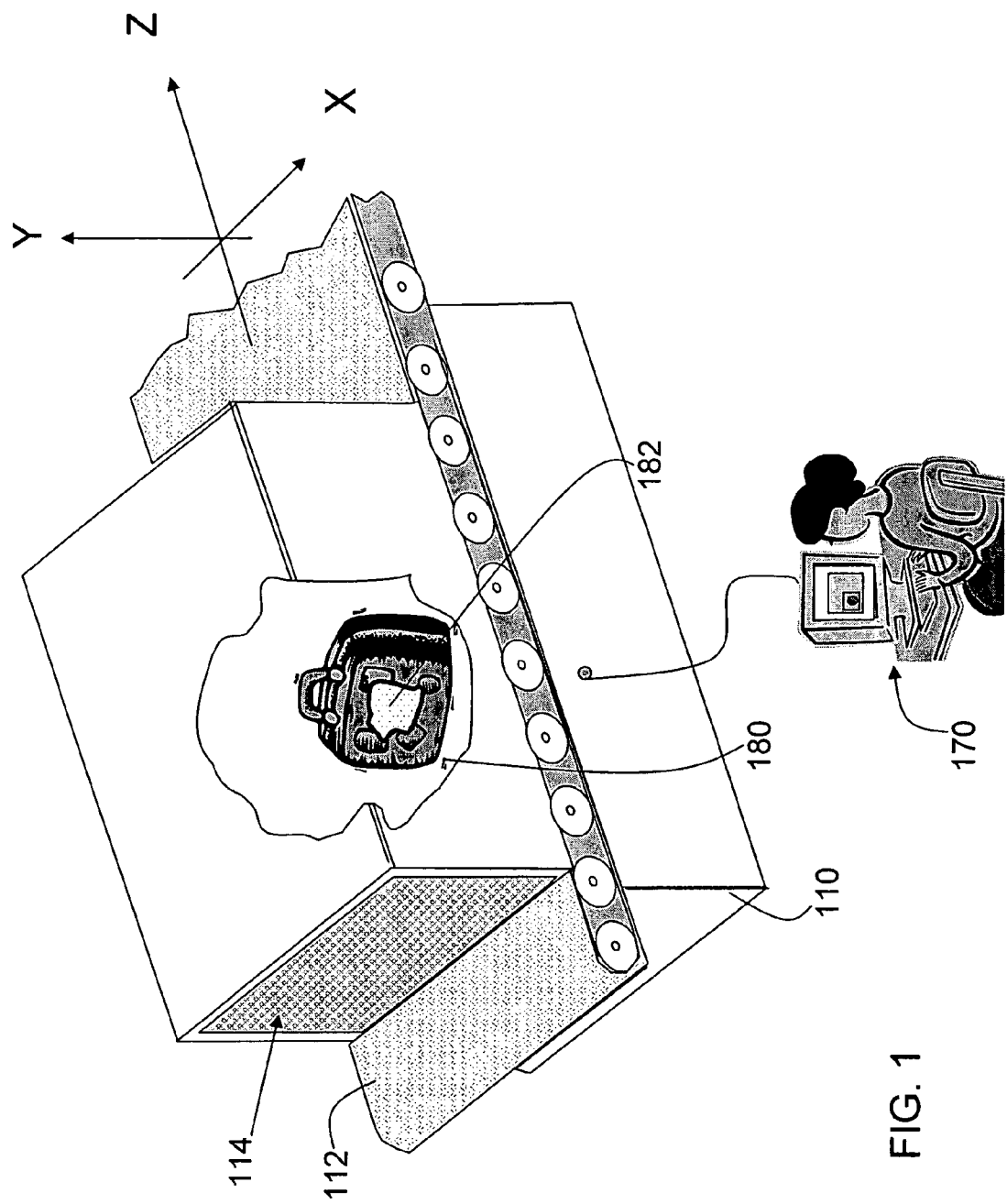
FIG. 1 is sketch of an explosive detection system in which an embodiment of the invention may be employed.

The inventors have appreciated that an improved inspection system may be formed with improved material identification capabilities. The improvements may be in the size, speed, cost or accuracy of the system.

In some embodiments, the improved inspection system uses an angular analysis system that selectively measures radiation at a specified angle. In one aspect, an improved angular analysis system may result from independently positionable source and detector assemblies that allow the angular analysis system to be focused on a region of an item under inspection by relative motion of the source and detector assemblies parallel to a plane holding an item under inspection. This configuration allows the angular analysis system to have a relatively small size and enables it to be practically used in environments where space is constrained. For example, such a system may be used in a baggage inspection system at an airport. It may be installed in an existing inspection bag room or as part of an in-line conveyor system without removing walls, raising ceilings or otherwise making extensive physical modifications to airport buildings.

In another aspect, speed of inspection may be improved by synchronizing motion of the source and detector assembly with motion of an item under inspection while a measurement is made. Because a conveyor carrying the items does not need to stop and restart for each item to be inspected, the inspection system may have a higher throughput. Items to be inspected can be continuously inspected at a rate matching the rate at which suspicious objects are identified by a first level inspection system.

In another aspect, the speed of the angular analysis system may be increased by providing a collimator configuration that increases the amount of radiation reaching the detector without unreasonably decreasing the angular resolution of the system. Such a system reduces the time required to acquire data with a signal to noise ratio adequate for an accurate determination of material properties.

These aspects may also reduce system cost. For example, providing a simple mechanism to an angular analysis system on suspicious regions of an item under inspection may reduce the overall cost of the system.

Costs may also be reduced in other ways. In another aspect, the angular analysis system can be simply reconfigured to selectively measure radiation emanating at different angles from a region of an item under inspection. The same detector can be used to measure radiation at multiple angles, reducing the overall cost of the system.

Aspects of the angular analysis system may also increase the accuracy of the system. Facilitating measurements of radiation emanating at different angles may increase the accuracy of the system by allowing a material to be analyzed based on radiation emanated at an angle that reveals the most useful information for analysis. In addition, the small size of such a system allows it to be readily used in conjunction with systems employing other inspection technologies. Using such systems together may significantly improve the accuracy with which the overall inspection system operates.

These and other aspects of an inspection system are described below using an explosive detection system as an example. Such a system, for example, may be used at an airport to inspect checked luggage, carryon baggage or other similar items. However, the invention is not limited to this example embodiment.

FIG. 1 illustrates an explosive detection system 110 according to an embodiment of the invention. Explosive detection system 110 includes a mechanism to move items under inspection through the system. In this example, conveyor 112 moves item under inspection 180.

Conveyor 112 runs through a tunnel 114. Tunnel 114 is formed from a housing or other suitable structure. As will be described in more detail below, explosive detection system 110 includes equipment within tunnel 114 that irradiates an item under inspection with x-rays and measures radiation that has interacted with the item under inspection. These measurements are used to aide a determination of whether the item under inspection contains an explosive.

Though a single housing is shown in FIG. 1, in some embodiments, the equipment may be positioned in multiple housings. Those housings may be coupled in any suitable way, such as by a conveyor system. Moreover, the housing may be in any desired form and may be omitted in some embodiments.

Explosives are one example of the types of objects that an inspection system may detect and the invention is not limited to use in conjunction with systems that detect explosives. More generally, an inspection system used as part of a security system may screen items under inspection and indicate whether each item may contain detect drugs, illicit currency, weapons or other contraband items. Though, the invention is not limited to use in conjunction with such security systems. It may be used in conjunction with any type of system that determines material properties, such as systems that detect valuable materials in mining or recycling operations.

In the example of FIG. 1, item under inspection 180 is illustrated as a suitcase with an object inside of it forming a suspicious region 182. Explosive detection system 110 operates to determine, with a high degree of accuracy, whether suspicious region 182 is formed by an explosive material inside item under inspection 180. The overall output of explosive detection system 110 is an indication that item under inspection 180 either contains no explosives and is "clear" or possibly contains an explosive and requires an "alarm."

As shown, the output of explosive detection system 110 is provided at an operator review station 170. A human operator monitoring operator review station 170 may make a determination of the appropriate processing required for an item under inspection based on the output of explosive detection system 110. That output instead or additionally may be processed by one or more computers as part of making a determination of whether an item under inspection is clear or is alarmed.

In the described embodiment, explosive detection system 110 includes two stages. A different inspection technology is used at each stage to make an overall determination that item under inspection 180 either is "clear" or requires an "alarm." One stage performs a first level inspection, which, for each item under inspection, indicates that the item is clear or that it contains a suspicious region. Those items containing suspicious regions are then transferred to the second level of inspection for a more accurate determination of whether the item is clear or requires an alarm.

Figure 2:
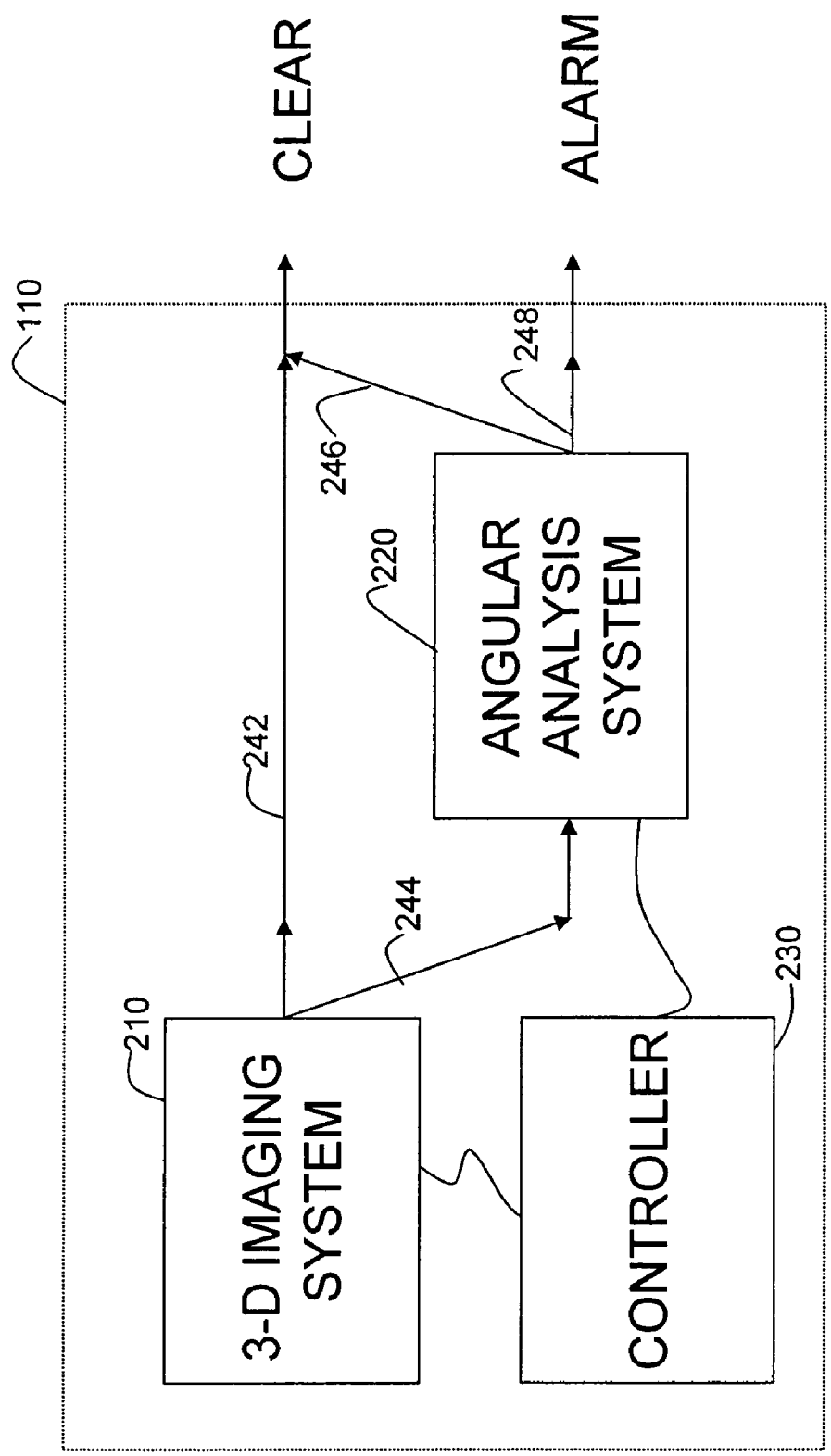
FIG. 2 is a block diagram of an inspection system according to an embodiment of the invention.

FIG. 2 illustrates, in block diagram form, the construction of explosive detection system 110. Explosive detection system 110 includes a three-dimensional imaging system 210 and an angular analysis system 220. In this embodiment, three-dimensional imaging system 210 acts as a level 1 scanner to make an initial determination whether an item under inspection contains any suspicious regions. Angular analysis system 220 serves as a second level inspection system and determines properties of materials in each suspicious region. Information on the materials in the suspicious regions allows a more accurate indication of whether each suspicious region is either an explosive or an innocuous item.

In the embodiment shown, three-dimensional imaging system 210 and angular analysis system 220 are interconnected by a conveyor system. Here the conveyor system is shown to contain conveyors 242, 244, 246, and 248. If, upon initial inspection, three-dimensional imaging system 210 detects no suspicious regions within an item under inspection, the item under inspection is diverted to conveyor 242, causing the item under inspection to be "cleared." In the example of an explosive detection system used for an airport security system, cleared items may be loaded onto airplanes, returned to passengers for carry-on to an airplane or otherwise allowed to enter a secured area.

Alternatively, if three-dimensional imaging system 210 identifies one or more suspicious regions in an item under inspection, the item under inspection is diverted to conveyor 244. Conveyor 244 carries the item under inspection to angular analysis system 220 for a level 2 inspection.

As shown, three-dimensional imaging system 210 and angular analysis system 220 are both coupled to controller 230. Controller 230 provides a mechanism for information concerning an item under inspection to be passed from three-dimensional imaging system 210 to angular analysis system 220. Information passed from three-dimensional imaging system 210 to angular analysis system 220 may include the number and locations of suspicious regions identified by three-dimensional imaging system 210. Further, the information may include a preliminary indication of the type of threat object suspected or other information indicating why a region was indicated as a suspicious region by three-dimensional imaging system 210.

Angular analysis system 220 uses the information generated by three-dimensional imaging system 210 to identify locations within an item under inspection at which material properties should be measured. In the pictured embodiment, angular analysis system 220 makes measurements that reveal information on the properties of materials within the suspicious regions of the item under inspection. Explosive detection system 110 may then use this information to determine whether each suspicious region contains an explosive or other threat item or whether it contains an innocuous item. Such a determination may be made by a processor or other computer hardware within angular analysis system 220 that is suitably programmed. However, such processing may be performed in any suitable processor.

In the example described herein, angular analysis system 220 uses x-ray diffraction analysis to measure properties of the material in each suspicious region. Briefly, x-ray diffraction systems operate on the principal that x-rays are diffracted, or scattered, from a material at an angle that is related to the properties of that material. More specifically, x-rays are diffracted at an angle related to the energy of the x-ray and the spacing between the molecules in the material from which they are diffracted. Accordingly, the spectrum of x-rays diffracted at a particular angle from an object provides information about the type of material in that object. By matching the spectrum of scattered x-rays to a spectrum of a known explosive material or to a spectrum of a know innocuous material, angular analysis system 220 may provide information allowing a suspicious region identified by three-dimensional imaging system to be classified with higher confidence as a threat or as an innocuous item.

X-ray diffraction is described in the literature, including U.S. Pat. No. 6,118,850 to Mayo et al. entitled "Analysis Methods for Energy Dispersive X-ray Diffraction Patterns," issued Sep. 12, 2000, which is hereby incorporated by reference in its entirety. Angular analysis system 220 may perform analysis as described in that patent or in any other suitable way.

However, X-ray diffraction is not the only possible type of angular analysis. Some materials fluoresce when irradiated, which generates radiation with a spectrum characteristic of the material. By capturing radiation emitted at a particular angle, it may be possible to selectively receive radiation emitted from a suspicious region of an item under inspection. Analysis of the spectrum of the captured radiation may indicate the nature of the material in that suspicious region.

Regardless of the exact principle of operation of angular analysis system 220, the system includes a focusing system that allows radiation from a region of an item under inspection to be captured and analyzed. In operation, angular analysis system 220 is focused on one or more locations within each suspicious region identified by three-dimensional imaging system 210. Radiation emanating from these regions is captured and analyzed. Information obtained by this analysis is used to determine whether each suspicious region contains only innocuous material or contains material characteristic of a threat.

An item under inspection for which all suspicious regions are determined to contain only innocuous material is diverted onto conveyor 246. Items diverted onto conveyor 246 are thereafter process as cleared items. Conversely, if information generated by angular analysis system 220 indicates that one or more of the suspicious regions contains an explosive or other threat item, the item under inspection is alarmed. The alarmed item may be diverted onto conveyor 248, where the item under inspection is processed in the manner appropriate for an item containing an explosive or other contraband item. For example, alarmed items may be further inspected, including by a manual search, or may be destroyed or otherwise precluded from entering a secured area.

In the example of FIG. 2, three-dimensional imaging system 210 and angular analysis system 220 are shown as independent systems with controller 230 passing information between them to allow the overall system to make a determination about each item under inspection. Such an architecture is just one example of an architecture for explosive detection system 110. Acquisition of data and analysis of that data may be performed in any suitable hardware. For example, all data analysis could be performed in controller 230. In such embodiments, three-dimensional imaging system 210 may acquire data on an item under inspection and provide that data to controller 230. Controller 230 may analyze the data acquired by three-dimensional imaging system 210 to detect suspicious regions. Similarly, angular analysis system 220 may measure the spectrum of scattered radiation from an item under inspection and provide data describing the measured spectrum to controller 230. Controller 230 may thereafter analyze the measurements to determine whether an item under inspection should be processed as an alarmed item or processed as a cleared item.

Though, this is only an example of one partitioning of the data analysis and processing functions and other embodiments are possible. For example, three-dimensional imaging system 210 and angular analysis system 220 may be housed within the same physical unit or may be housed in separate physical units. They may be located relatively close together or maybe located in different physical locations and interconnected through a computer network or other communication medium.

In embodiments in which three-dimensional imaging system 210 and angular analysis system 220 are separate units linked by a conveyor system, it may be necessary to relate the coordinate system in which angular analysis system 220 measures properties of suspicious region to the coordinate system in which three-dimensional imaging system reports suspicious regions. In the pictured embodiment, because three-dimensional imaging system 210 and angular analysis system 220 are in separate locations, it is possible for an item under inspection to shift its position on the conveyor system as the item is moved from three-dimensional imaging system 210 to angular analysis system 220. Accordingly, angular analysis system 220 may be adapted to contain a system to register its coordinate system to that used by three-dimensional imaging system 210. An example of a suitable system is described in co-pending patent application Ser. No. 11/400,489, entitled "REGISTRATION SCHEME IN EXPLOSIVES DETECTION SYSTEM," and filed on Apr. 7, 2006, which is hereby incorporated in its entirety. However, any suitable mechanism to relate the coordinate systems may be used.

In operation, explosive detection system 110 may inspect a series of items. These items may be moved through three-dimensional imaging system 210 at a constant rate. Some portion of the items inspected at three-dimensional imaging system 210 may be cleared during first level inspection and then diverted on conveyor 242. However, the remainder of the series of items under inspection may be diverted on conveyor 244 for further analysis by angular analysis system 220. To provide high throughput for explosive detection system 110, angular analysis system 220 may process the items diverted on conveyor 244 at the same rate at which those items are processed by three-dimensional imaging system 210. Further, in some embodiments, angular analysis system 220 will perform measurements on items under inspection without stopping them as they move on conveyor 244. By avoiding the need to stop items within angular analysis system 220, the overall throughput of explosive detection system 110 may be increased. Accordingly, as described in more detail below, some embodiments of the invention provide an angular analysis system 220 that may perform measurements on items under inspection as they are moving on conveyor 244 through the angular analysis system 220.

In the embodiment of FIG. 2, three-dimensional imaging system 210 acts as a level 1 scanner. Explosive detection systems with level 1 scanners are known. Any suitable level 1 scanner may be used in explosive detection system 110. However, in this example, three-dimensional imaging system 210 is a helical scan CT system.

Figure 3:
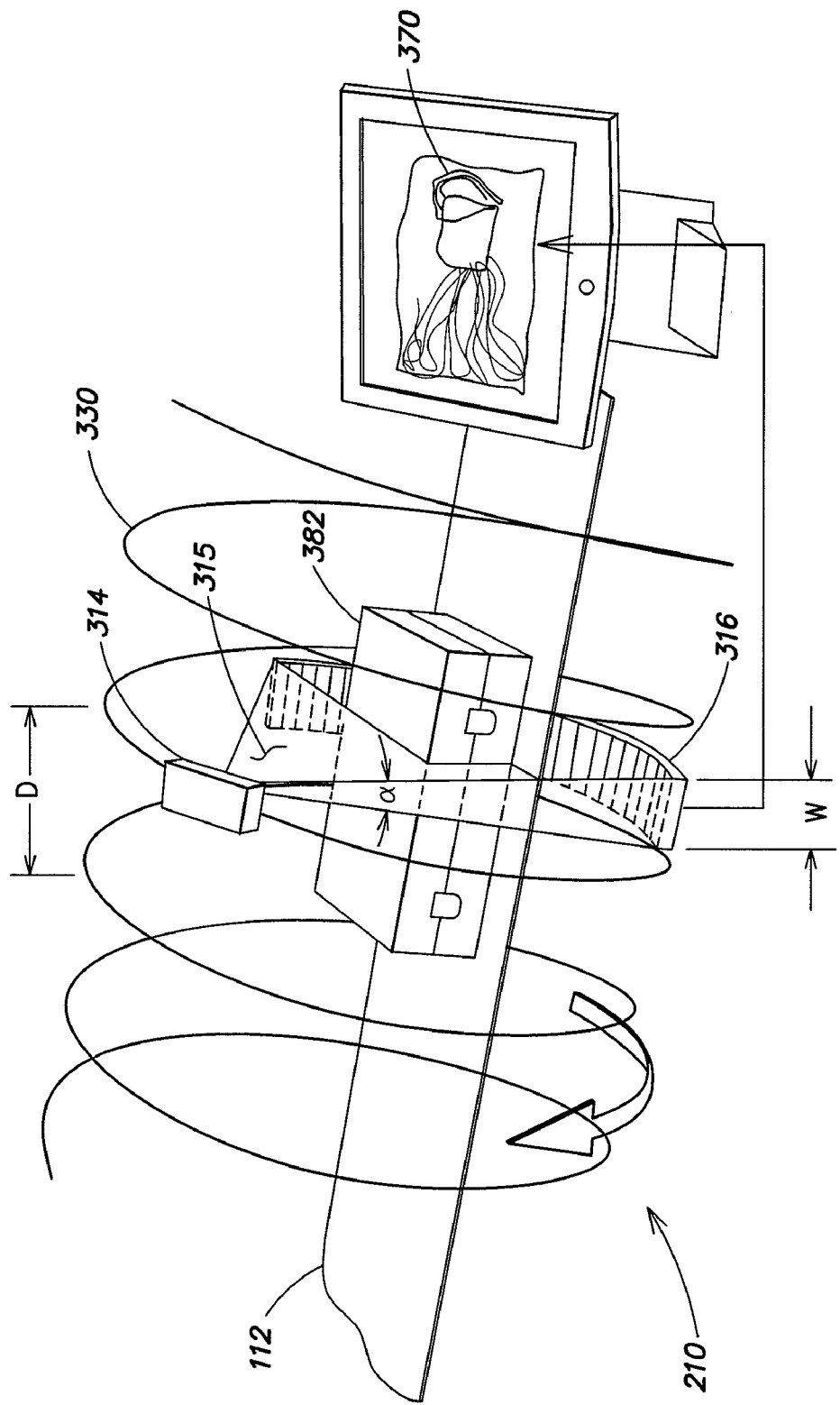
FIG. 3 is a sketch of a helical scan CT system, which may be used as the three-dimensional imaging system in the inspection system of FIG. 2.

FIG. 3 illustrates a helical scan CT system that may be used as a level 1 scanner in explosive detection system 110. As shown in FIG. 3, items under inspection, such as item 382, move continuously along a conveyor 112. As item under inspection 382 passes through three-dimensional imaging system 210, an x-ray source 314 and x-ray detector array 316 rotate around conveyor 112. Though the source 314 and detector array 316 rotate in a stationary plane perpendicular to conveyor 112, because item under inspection 382 is moving along conveyor 112, the source and detector array trace out a helical path 330 relative to item under inspection 382.

In the illustrated embodiment, x-ray source 314 and detector array 316 combine to measure the x-ray power passing through item under inspection 382. Such a measurement indicates the amounts various portions of the item under inspection 382 attenuated the x-rays. These attenuation measurements may be used as an indication of the density of regions of the item under inspection. In the system as shown, attenuation is determined for x-rays at a single energy level and suspicious regions are identified based on the shape and density of the region.

However, materials of different atomic number attenuate x-rays of different energies differently. Some x-ray imaging systems make multi-energy x-ray measurements to obtain information about the atomic number of the materials in the item under inspection. Thus, in some embodiments, three-dimensional imaging system 210 may identify suspicious regions in part based on their atomic number.

Regardless of whether single or multi-energy measurements are made, as in a conventional helical scan system, source 314 may have a beam angle α designed to intersect the entire width W of detector array 316. The speed of rotation of the source 314 and detector array 316 may be controlled relative to the speed of conveyor 112 such that the spacing D between loops of helical path 330 is sufficiently small that adequate data is collected on item under inspection 382 to allow computed tomographic reconstruction techniques to be used to form a three-dimensional image of item under inspection 382. With this configuration, an image of each item under inspection may be generated within three-dimensional imaging system 210 as items under inspection pass in a continuous stream along conveyor 112.

In the embodiment of FIG. 3, an image formed by three-dimensional imaging system 210 is illustrated graphically as image 370. Image 370 appears as it may be presented on a computer screen to an operator of three-dimensional imaging system 210. In some embodiments, the image formed by three-dimensional imaging system 210 may be presented graphically to a human operator who may then select suspicious regions for further analysis. However, in other embodiments, the image may be processed by a computer system without intervention of a human operator. Data analysis techniques to automatically recognize suspicious regions from measurements made with a three-dimensional imaging system are known. Such techniques, or any other suitable technique, may be used to identify suspicious regions within item under inspection 382.

Figure 4:
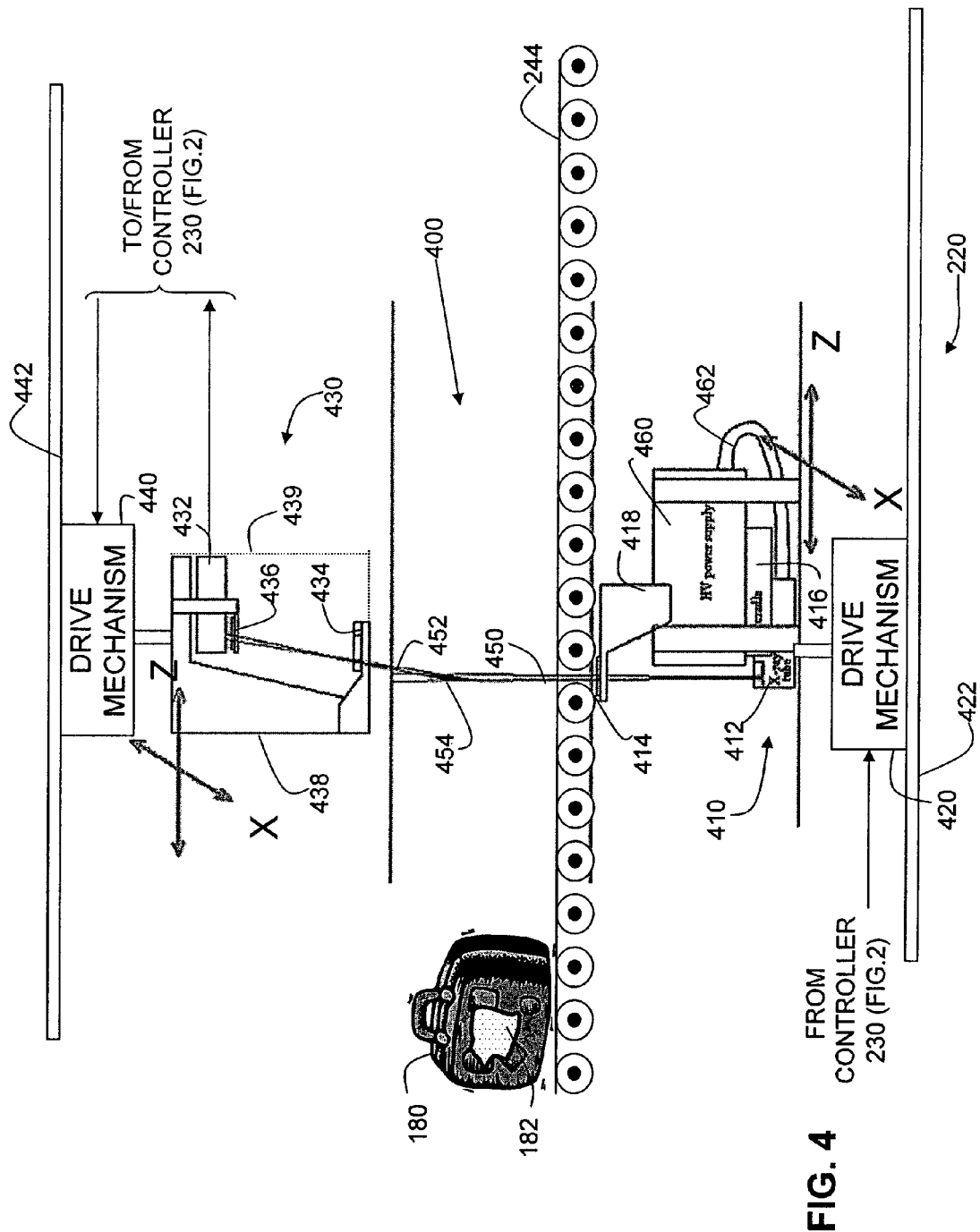
FIG. 4 is a side view of an X-ray diffraction system, which may be used as the angular analysis system in the inspection system of FIG. 2.

Those items under inspection containing suspicious regions are diverted to angular analysis system 220 (FIG. 2). Angular analysis system may be operated to focus on the suspicious regions to better identify whether they contain threat items or innocuous items. FIG. 4 illustrates details of a focusing system of angular analysis system 220 according to an embodiment of the invention.

In this embodiment, conveyor 244 moves an item under inspection 180 into an inspection region 400. Angular analysis system 220 is focused on one or more points within each suspicious region 182 identified as a result of level 1 scanning. As used herein, "focusing" means that the system is configured to receive radiation emanating from a selected region. In the configuration shown in FIG. 4, angular analysis system 220 is focused on focus region 454.

To gather information on suspicious region 182, item under inspection is moved on conveyor 244 into inspection region 400. Angular analysis system 220 is then adjusted to focus on a location within suspicious region 182 and radiation emanating from that location is gathered and analyzed. If information on other locations within suspicious region 182 is desired, the system is refocused and more data is collected. In some embodiments, two measurements are taken on each suspicious region, but any number of measurements may be taken. Once data is collected for one suspicious region, the system may be refocused on other suspicious regions.

In the pictured embodiment, angular analysis system 220 is an x-ray diffraction system. For an x-ray diffraction system, data is collected by radiating an item under inspection with x-rays. In the embodiment of FIG. 4, item under inspection 180 is radiated with pencil beam 450 of x-ray radiation. Pencil beam 450 is generated by an x-ray source. As can be seen in FIG. 4, pencil beam 450 passes through focus region 454.

In the illustrated embodiment, angular analysis system 220 includes a source assembly 410 that generates pencil beam 450. Source assembly 410 includes an x-ray tube 412.

X-ray tube 412 is powered by high voltage power supply 460. In some embodiments, high voltage power supply 460 is selected to power x-ray source 412 to emit radiation at a range of energies. The upper limit of that range is set by the voltage of high voltage power supply 460. In some embodiments, high voltage power supply 460 has an upper range of about 130 keV. In one embodiment, high voltage power supply 460 has a voltage of approximately 100 keV. A maximum supply of voltage of about 100 keV or less has been found to provide adequate energy that detector 432 may make a measurement without introducing an unreasonable amount of noise that interferes with measurements.

In the illustrated embodiment, power supply 460 is not mounted to source assembly 410. It supplies power to x-ray tube 412 through flexible cable 462 that allows source assembly 410 to move relative to power supply 460. Such a configuration allows power supply to be mounted in any suitable location and may be separated from the remainder of the system by distance, shielding or in any other suitable way.

Radiation leaving x-ray tube 412 is collimated into a pencil beam by collimator 414. Collimator 414 may be a material opaque to x-rays, such as titanium, having a small aperture, such as a pinhole. Collimator 414 is held by support member 418, which may be coupled to x-ray tube 412. In this embodiment, collimator 414 has a fixed position relative to x-ray tube 412 such that source assembly 410 emits pencil beam 450 perpendicular to conveyor 244. As shown, source assembly 410 may move in the directions labeled X or Z to position the source assembly 410 so that pencil beam 450 passes through any desired focus region. To position beam 450, source assembly 410 is coupled to drive mechanism 420. In operation, drive mechanism 420 is controlled, such as by commands sent from controller 230, to position pencil beam 450 such that it passes through a suspicious region 182 within item under inspection 180. Drive mechanism 420 may be any suitable drive mechanism, including an electric linear motor, an electric rotating motor or a hydraulic actuator.

In this embodiment, drive mechanism 420 is shown coupled to track 422 that guides drive mechanism 420 in the Z direction. A similar track (not shown) may be included to guide drive mechanism 420 as it moves in the X direction. However, any suitable mechanical support structure may be used to movably retain source assembly 410. In the illustrated embodiment, drive mechanism 420 may position source assembly 410 at any desired position in the X-Z plane below inspection area 400.

In the example of FIG. 4 in which angular analysis system 220 is an x-ray diffraction system, measurements are made by collecting radiation diffracted at a specific angle relative to pencil beam 450. In the configuration illustrated in FIG. 4, diffracted radiation 452 emanating from focus region 454 is measured and analyzed.

Information is gathered on the material within focus region 454 using detector assembly 430. Detector assembly 430 includes a detector 432. In this embodiment, detector 432 may be a high performance germanium detector. Detector 432 may be chilled to increase its sensitivity. In some embodiments, a range of measurements may be made using a single detector. However, any suitable detector or detectors may be used.

The output of detector 432 may be coupled to controller 230 (FIG. 2) or other suitable data processing device. This output may be processed using x-ray diffraction techniques as described above and as described in more detail below to identify the type of material within suspicious region 182.

As shown in FIG. 4, detector 432 is positioned to receive radiation 452 emanating from focus region 454. Radiation 454 reaches detector 432 because it is emanating from focus region 454 at an angle that allows it to pass through both aperture plates 434 and 436. As shown, aperture plates 434 and 436 have relatively narrow apertures and are held apart by support member 438 at a sufficient distance that only radiation traveling in a relatively small range of angles can pass through aperture plates 434 and 436. Detector assembly 430 contains shielding 439 that blocks radiation from reaching detector 432 other than through aperture plates 434 and 436.

The size, shape and relative position of aperture plates 434 and 436 define a field of view for detector 432. The intersection of this field of view for detector 432 with pencil beam 450 defines a focus region 454 on which a measurement is taken. By controlling the position of detector assembly 430 relative to source assembly 410, the point at which this field of view intersects pencil beam 450 can be controlled, thereby controlling the location of focus region 454.

Accordingly, detector assembly 430 is coupled to a drive mechanism 440, which allows it to be positioned to achieve the desired focus. Drive mechanism 440 may be mounted on track 442 or mounted in any other suitable way that allows detector assembly 430 to be positioned so that angular analysis system 220 images the desired focus region.

In the pictured embodiment, controller 230 (FIG. 2) provides commands to drive mechanism 420 and drive mechanism 440 to position source assembly 410 and detector assembly 430 such that focus region 454 coincides with a suspicious region 182. If multiple measurements are desired within one suspicious region, information may be acquired from detector 432 with the source assembly 410 and detector assembly 430 positioned to focus at the desired location within suspicious region 182. Thereafter, either or both of source assembly 410 and detector assembly 430 may be repositioned to focus angular analysis system 220 on a different location within suspicious region 182.

In some embodiments, a single measurement may be made for each suspicious region 182. In other embodiments, controller 230 may control angular analysis system 220 to take a second measurement within suspicious region 182. Any number of measurements may be taken within a suspicious region.

Regardless of the number of measurements taken on each suspicious region, if an item under inspection 180 contains multiple suspicious regions, controller 230 (FIG. 2) may control drive mechanisms 420 and 440 to sequentially position source assembly 410 and detector assembly 430 to focus on each suspicious region.

In some embodiments, diffracted x-rays will have sufficiently low flux that data must be captured over a finite data capture period in order to capture enough x-ray photons for reliable analysis. If conveyor 244 is moving an item under inspection relative to source assembly 410 and detector assembly 430 during this data capture period, the system will be focused on different regions of the item under inspection at the start and end of the data capture period. Capturing data in this fashion may not be sufficiently accurate for some applications. Therefore, in some embodiments, controller 230 may generate commands to the conveyor system to stop conveyor 244 while data is being captured on one region of an item under inspection.

Even if conveyor 244 is stopped for a measurement, it is not necessary in all embodiments that source assembly 410 and detector assembly 430 be held stationary. For example, while detector 432 is capturing data, in some embodiments source assembly 410 and detector assembly 430 may move slightly relative to item under inspection 180. Such slight motion, sometimes called "dither," may average out measurement noise and increase the accuracy with which measurements are made.

Further, whether or not dither is employed in a measurement, it is not necessary that item under inspection be held stationary while data is being acquired. In some embodiments, conveyor 244 may move item under inspection 180 through inspection region 400 while measurements are being made on item under inspection 180. Because both source assembly 410 and detector assembly 430 may move in the Z direction, source assembly 410 and detector assembly 430 may move in synchronization with item under inspection 180. In this way, the relative position of item under inspection 180 to source assembly 410 and detector assembly 430 may be maintained while a measurement is being made even though item under inspection 180 moves.

If the speed of conveyor 244 is such that an item under inspection does not pass through inspection area 400 faster than the time required to take measurements on the suspicious regions in the item under inspection, conveyor 244 does not have to be stopped. By taking measurements without stopping conveyor 244, no time is lost starting and stopping conveyor 244. Furthermore, by continuously inspecting items in angular analysis system 220 at the rate at which they are processed in three-dimensional inspection system 210, items under inspection may flow continuously from the level 1 scanner, which increases the overall throughput of explosive detection system 110.

With the embodiment of FIG. 4, the full range of measurements that can be made on item under inspection 180 while stopped can also be made as it moves through inspection region 400. For example, to reposition source assembly 410 and detector assembly 430 for measurements on a second suspicious region, one or both of the source assembly 410 and detector assembly 430 may be moved at a rate different than the item under inspection to focus angular analysis system 220 on the desired location within item under inspection 180. Likewise, to collect data while dithering the source and detector, the source and detector can be synchronized to, on average, move at the same speed as conveyor 244, but to have an instantaneous speed at any given time that is slightly above or slightly below the speed of conveyor 244.

Figure 5:
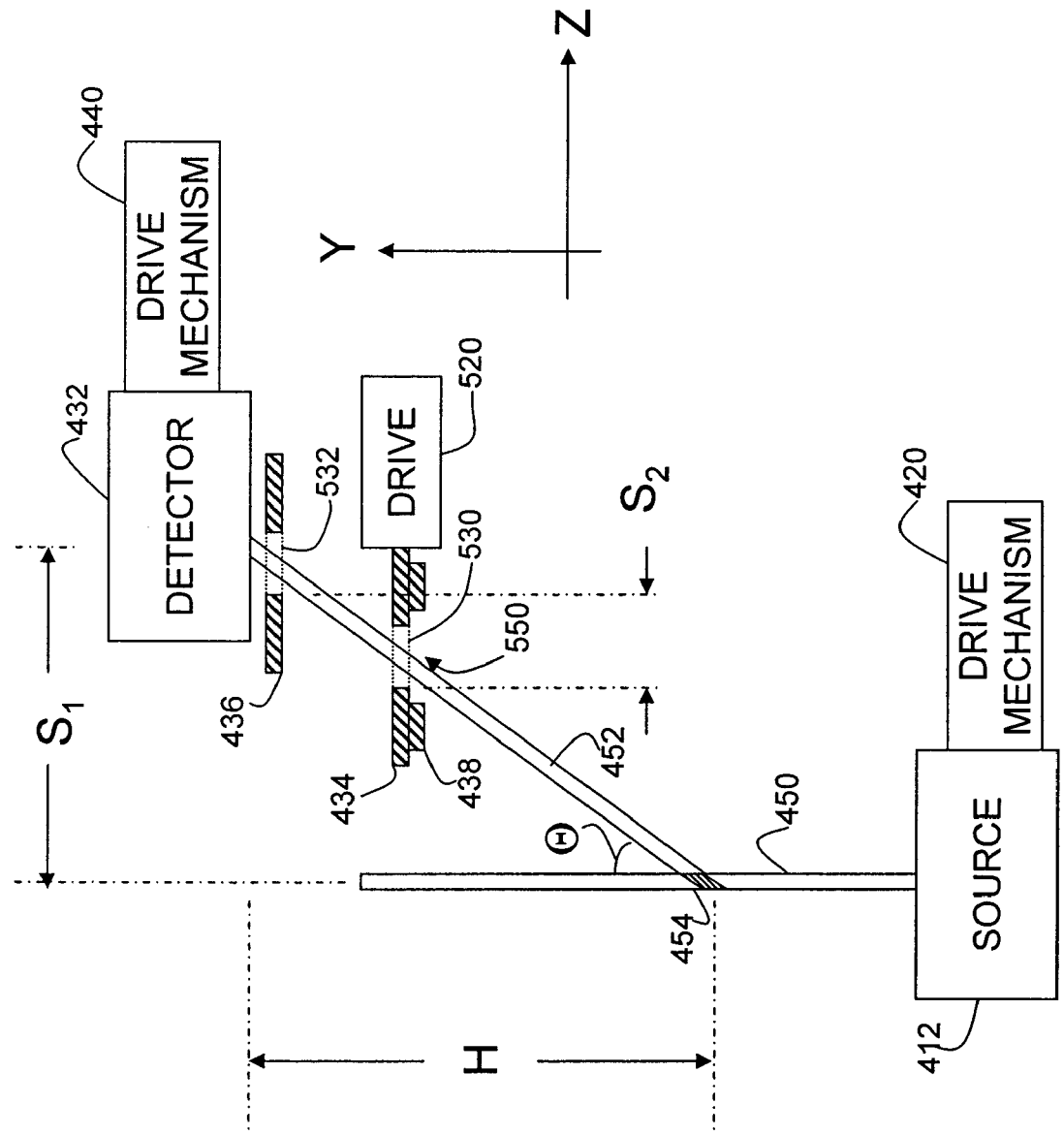
FIG. 5 is a sketch useful in understanding adjustment of the X-ray diffraction system of FIG. 4.

FIG. 5 shows in greater detail how the relative positioning of source assembly 410 and detector assembly 430 may be used to focus angular inspection system 220 on the specific focus region 454 and to selectively process radiation emanating at a defined angle. In the pictured embodiment, angular analysis system 220 may be focused in three dimensions and select an examination angle with only movement in two dimensions. Those two dimensions are parallel to conveyor 244, which allows for a compact system.

FIG. 5 shows the system in cross section as seen in the Y-Z plane. As described above in connection with FIG. 4, the source and the detector can be positioned independently within the X-Z plane. Focus region 454 may be positioned at any point in the X-Z plane by positioning source 412 below the desired location. In the illustrated embodiment, detector 432 is positioned at the same X location as source 412. Then, detector 432 is positioned in the Z direction so that radiation 452, diffracted at a desired angle, $\Theta$, from focus region 454 passes through the aperture plates 434 and 436.

Once this relationship between source 412 and detector 432 is set, focus region 454 can be translated to any location in the X-Z plane by translation of source 412 and the detector 432 in unison. As the source and the detector move together, focus region 454 will move a corresponding amount.

In the embodiment illustrated, the relative Y position of focus region 454 may be controlled by differential movement of source 412 and the detector 432. As shown in FIG. 5, focus region 454 is at a distance H in the Y direction below detector 432. The magnitude of H is related to the relative displacement in the Z direction of detector 432 from source 412. This relative displacement is indicated as $S_1$. By increasing $S_1$, the magnitude of H will increase, lowering focus region 454. Conversely, decreasing $S_1$ will raise focus region 454. Drive mechanisms 420 and 440 can be controlled to position source 412 and detector 432 to increase or decrease $S_1$ and position focus region 454 as desired.

Furthermore, the focusing system of angular inspection system 220 also may be constructed to allow the angle E to be simply controlled. As shown in FIG. 5, the angle $\Theta$ is controlled by the distance $S_2$ separating apertures 530 and 532. Increasing $S_2$ causes an increase in the angle $\Theta$. Conversely, decreasing $S_2$ causes a decrease in the angle $\Theta$.

By coupling aperture plate 434 to a drive mechanism 520, the angle $\Theta$ may be varied automatically, such as under control of a software program on controller 230. As will be described below in conjunction with FIGS. 7A and 7B, it may be desirable to make measurements on the same region of an item under inspection at different angles or to set the angle dynamically based on information about an item under inspection.

Drive mechanism 520 may be used to alter the spacing $S_2$ in any suitable way. Aperture plate could be moved in the Z direction to directly vary the distance $S_2$.

However, in some embodiments, drive mechanism 520 may move aperture plate 434 in the X direction. In such embodiments, aperture plate 434 may contain multiple apertures, located at different Z distances from the edge of the plate. Moving aperture plate 434 in the X direction may expose a different aperture through opening 550 in support member 438, thereby changing $S_2$. Translation in the X direction to vary the properties of the aperture in this fashion may also allow properties of the aperture other than its Z position to be easily controlled, as described below in conjunction with FIGS. 6A and 6B.

In the illustrated embodiment, the source and detector have independent positioning systems, allowing both the relative X and Z position of the source and detector to be controlled. However, in some embodiments, source 412 and detector 432 are controlled so that they have the same X position. In such embodiments, it is not necessary for the source and detector to have completely independent positioning systems. Simplified operation or construction may be possible by having the X positioning systems of the source and detector electrically or mechanically coupled so that the source and detector move together in the X direction.

Regardless of whether a simplified positioning system is used, angular analysis system 220 has a compact focusing system, allowing the overall system to be small and relatively low cost. The focusing system can control the coordinates of the focus region in X, Y, Z and $\Theta$ using only motion in the X-Z plane. Further, the focusing system does not require components that extend significantly further in the X-direction or Y-direction than inspection region 400 (FIG. 4). Moreover, it does not require space above or below inspection region 400.

Such a focusing system compares favorably to systems using a C-arm to couple the source assembly and detector assembly. Systems with C-arms need to provide additional clearance above, below and on the side of the inspection region to accommodate the C-arm in any focus position.

Figure 6A:
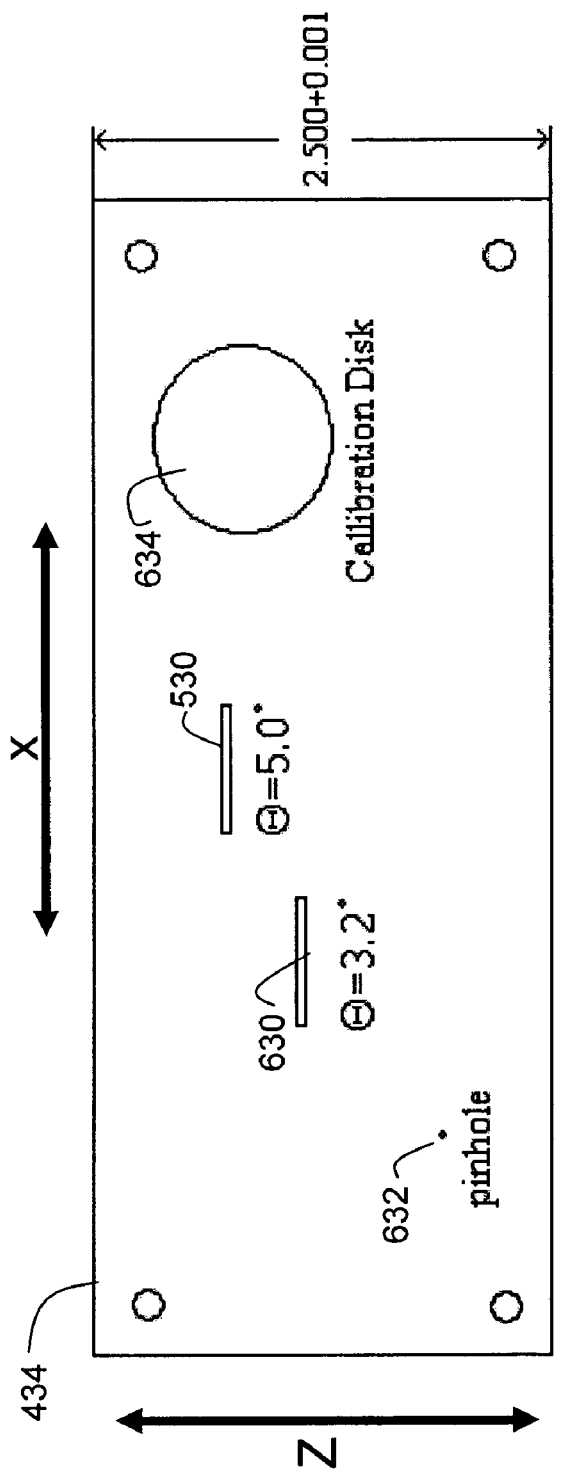
FIG. 6A is a top view of an aperture plate of the X-ray diffraction system of FIG. 4.
Figure 6B:
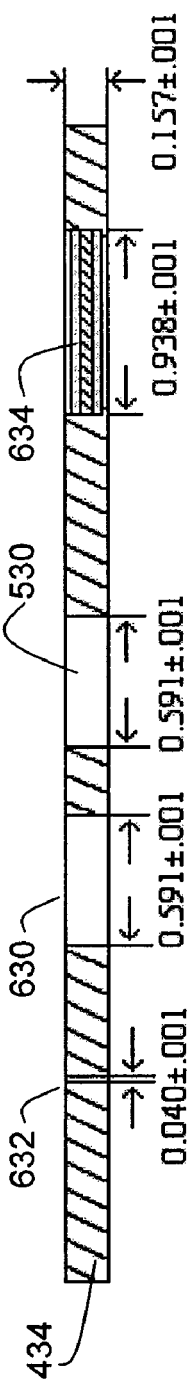
FIG. 6B is a side view of the aperture plate of FIG. 6A.

Turning to FIGS. 6A and 6B, additional details of aperture plate 434 may be seen. Aperture plate 434 may be constructed from a material that blocks radiation from reaching detector 432 (FIG. 4) except that radiation passing through an aperture in aperture plate 434.

In the embodiment of FIGS. 6A and 6B, aperture plate 434 contains multiple apertures. Here, apertures 530 and 630 are shown for use in acquiring radiation from specified angles. As described above, motion of aperture plate 434 in the X direction positions one of the apertures in the aperture plate 434 within opening 550. The aperture on aperture plate 434 positioned within opening 550 (FIG. 5) dictates characteristics of radiation reaching the detector 432. For example, apertures 530 and 630 have different positions in the Z direction, but otherwise have similar characteristics. In this embodiment, aperture 630 is positioned in the Z direction to allow radiation at an angle of 3.2° to reach detector 432. Conversely, aperture 530 is positioned in the Z direction to allow radiation at an angle of 5° to reach detector 432.

In some embodiments, apertures with different shapes or other characteristics may be included on aperture plate 434. However, in this embodiment, apertures 530 and 630 are both shown as slits elongated in the X direction. The slits are narrow in the Z direction. In an embodiment such as is shown in FIG. 5 in which the detector 432 is offset from source 412 in the Z direction, an aperture that is narrow in the Z direction provides good angular resolution. Good angular resolution, in this context, indicates that radiation diffracted at a relatively narrow range of angles is allowed to reach detector 432. Good angular resolution is desirable in some embodiments because the spectrum of diffracted radiation is dependent on the angle at which the radiation is measured. If radiation diffracted at multiple angles simultaneously reaches detector 432, multiple spectra may be superimposed in the measured radiation and it may become difficult to detect a single spectrum associated with a specific type of material within focus region 454.

However, providing a narrow aperture restricts the X-ray photon flux at detector 432. For detector 432 to make an accurate measurement, it must capture a sufficient number of X-ray photons. By reducing the X-ray photon flux, the data capture time may need to be increased, which may also be undesirable in some embodiments. However, to offset a decrease in X-ray photon flux by making aperture 530 and 630 narrow in the Z direction, apertures 530 and 630 may be elongated in the X-direction. Though elongating apertures 530 and 630 in the X direction decreases the spatial resolution with which focus region 454 may be specified, the inventors have appreciated that an explosive detection system 110 is less sensitive to a decrease in spatial resolution than to a decrease in angular resolution. Accordingly, in some embodiments, a slit-shaped aperture provides a desirable compromise between resolution and data acquisition time.

Nonetheless, it should be appreciated that the slit-shaped apertures as shown for apertures 530 and 630 are representative of the shapes that may be used to form apertures in plates 434. For example, apertures 530 and 630 may be shaped as ovals, circles or in any other suitable shapes.

Aperture plate 434 may also include apertures with characteristics that affect operating parameters of angular analysis system 220 other than the angle of radiation allowed to reach detector 432. For example, aperture plate 434 may be constructed with an aperture to hold a calibration disk 634. Calibration disk 634 may be a printed circuit board or other substrate coated with materials that emit radiation at specific energies when radiated by X-ray energy of the type emitted by source 412. Materials having these properties are known in the art, and any suitable materials may be used to construct calibration disk 634.

When calibration disk 634 is incorporated into aperture plate 434, it provides an easy mechanism for calibration of detector 432. Aperture plate 434 may be moved to position calibration disk 634 in opening 550 (FIG. 5). Calibration disk 634 may then be irradiated by beam 450. Because radiation emitted by calibration disk 634 has a known energy spectrum, the output of detector 432 in response to energy of this known spectrum may be used to calibrate detector 432.

As another example of the type of aperture that may be included on aperture plate 434, pin hole 632 is shown. Aperture plate 434 may be moved to position pin hole 632 within opening 550. Pin hole 632 may have a Z position in aperture plate 434 such that when it is positioned in opening 550, it will be aligned with aperture 532 (FIG. 5). With this alignment, radiation of X-ray source 412 will reach detector 432 only if source 412 and detector 432 are aligned in the X-Z plane. Accordingly, pin hole aperture 632 may be used to align source 412 and detector 432. Alternatively, pin hole aperture 632 may be used to measure the strength of radiation passing through an item under inspection without being scattered. Being able to measure the strength of radiation passing through an item under inspection in this way may provide additional information for analyzing a suspicious region.

To avoid saturating detector 432 for straight-through measurements, pin hole 632 may be laser drilled or otherwise made very small. If the material from which aperture plate 434 is constructed is to brittle to allow a sufficiently small pin hole to be formed, pin hole 632 may be provided with a small diameter by inserting a plug of a softer material, such as gold or lead, in which a small pin hole may be formed.

Figure 7B:
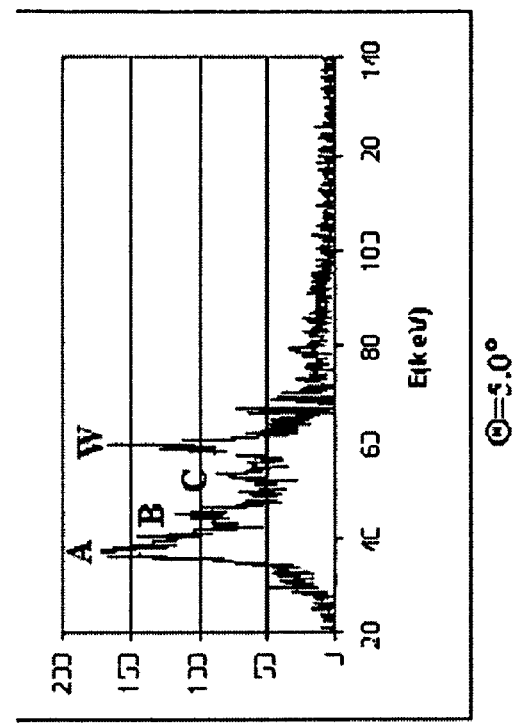
FIG. 7B is a sketch of an energy spectrum measured at a second angle with the X-ray diffraction system of FIG. 4.
Figure 7A:
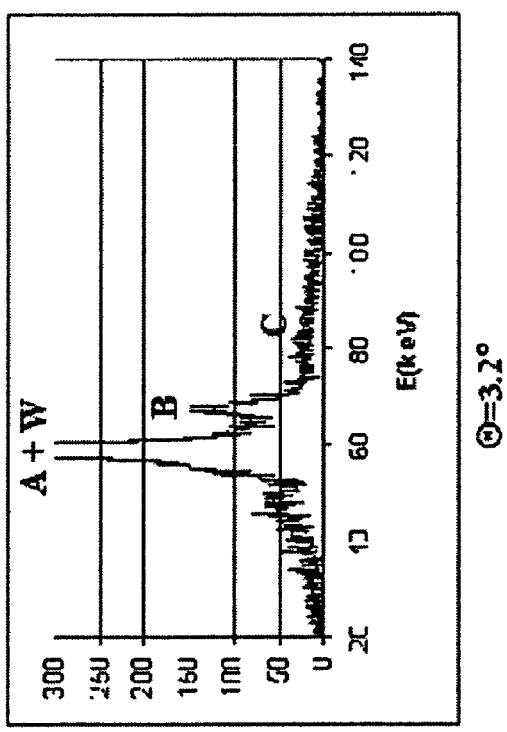
FIG. 7A is a sketch of an energy spectrum measured at a first angle with the X-ray diffraction system of FIG. 4.

Turning to FIGS. 7A and 7B, an example of the benefit of being able to automatically alter the properties of the aperture controlling radiation reaching detector 432 is provided. FIGS. 7A and 7B illustrate energy spectra from the same object but taken at different angles. The energy spectra of FIG. 7A was measured at an angle of 3.2° and, for example, may correspond to measurements made using aperture 630. FIG. 7B is representative of an energy spectrum taken at an angle of 5° and, for example, may represent a measurement taken with aperture 530.

In FIG. 7B, four readily identifiable peaks in the spectrum are visible. The peaks are labeled A, B, C and W. In this example, the peak labeled W represents energy from X-ray source 410 that is not diffracted. Accordingly, the peak labeled W appears at approximately 60 keV in both of the spectra of FIGS. 7A and of 7B. The other peaks, labeled A, B and C appear at energies that are dependent on the measurement angle because they have been diffracted. These peaks may provide a signature characteristic of a specific material of interest.

As shown in FIG. 7A, when the measurement is made at 3.2°, it is difficult to recognize the signature of that material. The peak identified as A is indistinguishable from the peak identified as W. Also, the peak identified as C is small and largely indistinguishable from noise associated with the measurement. Though the peak identified as B is readily observable, identifying a single peak in the spectrum may not provide accurate recognition of the material. In contrast, FIG. 7B shows that when X-rays scattered at an angle of 5° are measured for this material, three readily recognizable peaks identified as A, B and C appear in the spectrum. The peak A is separated in energy form the peak W in the spectrum of FIG. 7B and is therefore more readily recognizable than in FIG. 7A. Also, the peak identified as C is larger in comparison to the noise and also more readily identified.

Comparison of FIGS. 7A and 7B demonstrates that in some scenarios some measurement angles will be more suited for identifying a specific material than others. Appreciation of the phenomenon that different materials will be easier to recognize for measurements taken at different angles in combination with the ease of automatically altering the measurement angles provides by the system of FIGS. 4 and 5 gives rise to a novel process for operating an explosive detection system, such as explosive detection system 110 (FIG. 1). The process is illustrated by FIG. 8.

Figure 8:
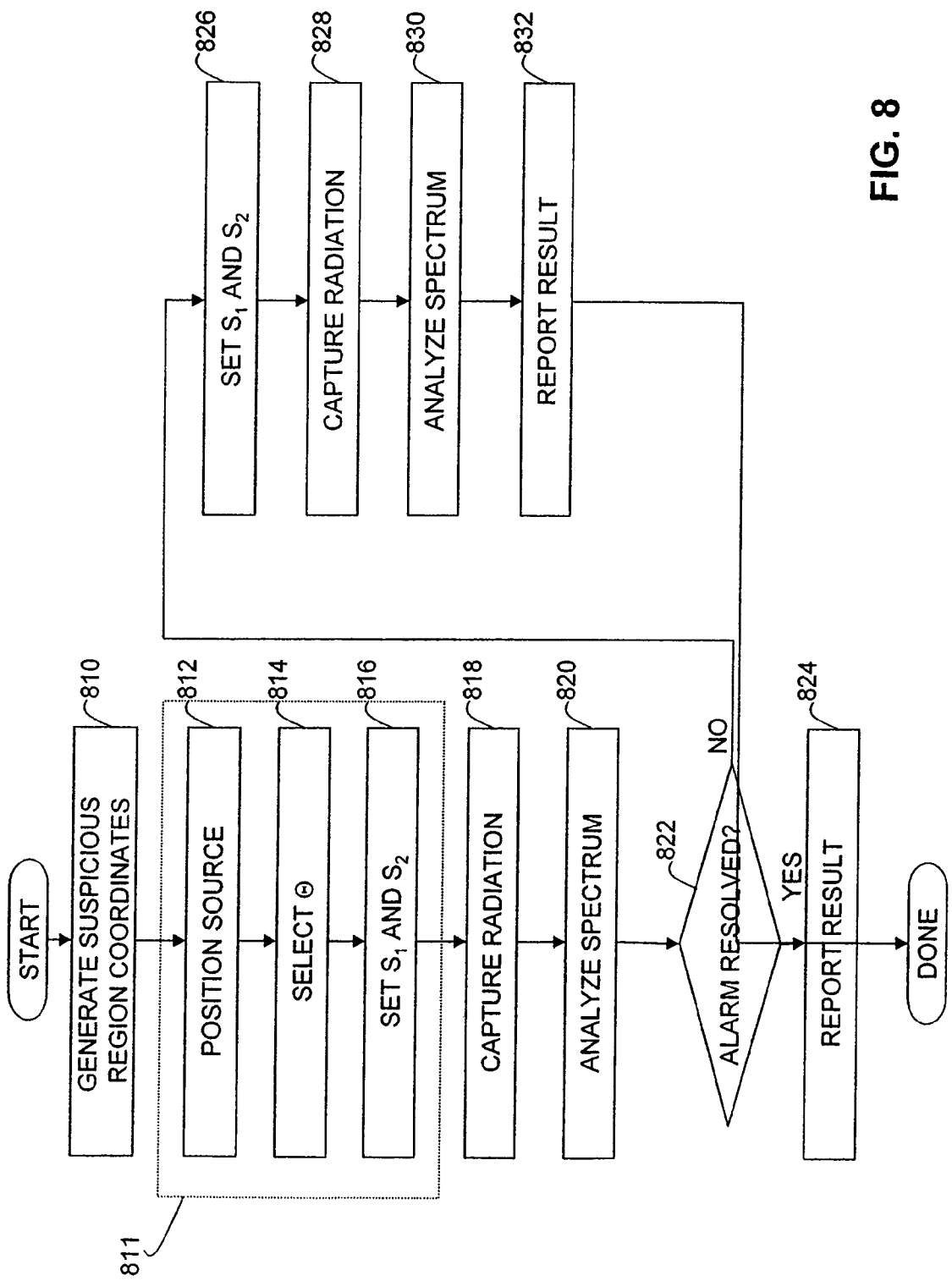
FIG. 8 is a flow chart illustrating operation of the X-ray diffraction system of FIG. 4.

The process of FIG. 8 begins at block 810 where coordinates of suspicious regions are generated. In explosive detection system 110, coordinates of suspicious regions may be generated by three-dimensional imaging system 210. However, the suspicious regions may be identified in any suitable way.

The coordinates generated at block 810 are used in sub-process 811 during which an angular analysis system is focused to measure a property of the material within a suspicious region. In the example in which the process of FIG. 8 is performed in explosive detection system 110, sub-process 811 is performed by providing coordinates of regions within the suspicious regions at which X-ray diffraction measurements are made.

At block 812 an X-ray source is positioned below the specific region in which material properties are to be measured.

The process continues to block 814 where a measurement angle is selected. Any suitable approach may be used to select a measurement angle. In situations where level one scanning provides information indicating the nature of the material in the suspicious region, such as for example if dual energy measurements indicate an atomic number, information may be available indicating the measurement angle most likely to produce a readily recognizable spectrum if the suspected material is present. In other embodiments, or when material information is not available, a measurement angle may initially be selected by default.

In setting the measurement angle at block 814, it is not necessary that the measurement be intended to identify a threat material. For example, when level 1 scanning indicates a suspicious region because the level 1 system can not reliably determine whether the region contains an innocuous plastic case or a plastic explosive, the measurement angle may be set to capture a spectrum in which the explosive may be readily recognized or, the measurement angle may be set to capture a spectrum in which the innocuous plastic case may be readily identified. Determining that either the suspicious region contains a threat material or an innocuous material may allow a more accurate determination of whether the item under inspection should be alarmed.

Once the measurement angle is selected, the process continues to block 816. At block 816, the components of the focusing system of angular analysis system 220 are positioned to provide the desired focus in height and angle. As shown in FIG. 5, drive mechanism 520 may position aperture 530 to control the measurement angle. Drive mechanism 440 may position the detector assembly to focus angular analysis system 220 on a focus region 454 at the desired height.

The process then proceeds to block 818 where radiation scattered from the focus region is captured. The processing at block 818 may last until a sufficient number of scattered X-ray photons are captured to provide a reliable measurement. As described above, the processing at block 818 may be performed while conveyor 244 is stationary or may be performed while the source and detector assembly are moving with the motion synchronized to the motion of conveyor 244.

Once sufficient radiation is captured, the process continues to block 820 where the spectrum of the captured radiation is analyzed. As shown in connection with FIGS. 7A and 7B, spectrum analysis performed at block 820 may involve matching peaks in the radiation spectrum to patterns of peaks associated with previously-identified material. If a sufficiently high correlation between the peaks of the captured radiation spectrum and the radiation spectrum of a known material is achieved, the material in the focus region is identified. If the material in the focus region is identified, when processing reaches decision block 822, the alarm may be resolved. The alarm may be resolved by identifying either that all suspicious regions in the item under inspection contain only innocuous materials or that at least one of the suspicious regions contains a threat material. If either of these resolutions is achieved, processing continues to block 824 where the result is reported. The processing at block 824 may include notifying a human operator that a threat has been detected, diverting the item under inspection for further processing as a cleared or alarmed item, as appropriate, or taking any other suitable action.

Conversely, if processing at block 820 does not result in information that allows the alarm to be resolved, processing continues to block 826. For example, the radiation captured at block 818 may not have a spectrum with distinctive peaks that could be matched to stored spectra. At block 826, different values of $S_1$ and $S_2$ may be set. By setting different values of $S_1$ and $S_2$, radiation may be captured at a different angle, but in the pictured embodiment radiation is captured from the same focus region as at block 818.

With these new settings for $S_1$ and $S_2$, processing proceeds to block 828. At block 282, radiation is again captured. The spectrum of this radiation is analyzed at block 830. The processing at blocks 828 and 830 may be similar to that performed at blocks 818 and 820. However, the spectra of known material compared to the radiation captured at block 830 are spectra of radiation captured at the same measurement angle that was set at block 826. Even if analysis at block 820 did not resolve the alarm, processing at block 830 may resolve the alarm if the measurement angle set at block 826 results in a radiation spectrum with a more recognizable pattern of peaks or other features.

The results of the analysis performed at block 830 are reported at block 832. The processing of block 832 may be similar to the processing performed at block 824. However, if no resolution of the alarm was possible based on the analysis performed at block 830, the item under inspection may be passed on to a higher level inspection with an indication that the alarm was not resolved.

The processing pictured in FIG. 8 is one example of a process that may be performed with an explosive detection system such as explosive detection system 110. Though processing is illustrated as occurring in sequential process blocks, any suitable ordering of the process blocks may be used, including concurrent execution of one or more process blocks. Also, FIG. 8 presents a greatly simplified illustration of possible processing. For example, various process steps illustrated in FIG. 8 may be repeated to take multiple measurements on each suspicious region or to take measurements on multiple suspicious regions on an item under inspection.

Having thus described several aspects of at least one embodiment of this invention, it is to be appreciated various alterations, modifications, and improvements will readily occur to those skilled in the art.

The above-described embodiments of the present invention can be implemented in any of numerous ways. For example, in the described embodiment, the detector collimator included slits elongated in the X-direction and the source and detector were controlled to maintain the same X position. The same results could be achieved by forming apertures elongated in the Y direction and controlling the source and detector to have the same Y position. Thus, specific directions of motion are not a limitation on the invention.

Also, the embodiments may be implemented using hardware, software or a combination thereof. When implemented in software, the software code can be executed on any suitable processor or collection of processors, whether provided in a single computer or distributed among multiple computers.

Also, the various methods or processes outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, etc.) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An inspection system, comprising:
 a) a conveyor adapted to move items in a first direction;
 b) a source assembly comprising:
  i) an x-ray source adapted to irradiate an item on the conveyor; and
  ii) a source collimator positioned between the x-ray source and the conveyor;
 c) a first positioning mechanism adapted and arranged to move the source assembly in a second direction, transverse to the first direction;
 d) a detector assembly comprising:
  i) a detector; and
  ii) a detector collimator positioned between the detector and the conveyor;
 e) a second positioning mechanism adapted and arranged to move the detector assembly in the second direction, the second positioning mechanism adapted and arranged to be controlled in at least one direction independently of the first positioning mechanism; and
 f) a controller adapted to control the first and second positioning mechanisms to independently position the source and detector assemblies relative to the item to focus the inspection system on a region within the item on the conveyor and to move the source and detector assemblies in the first direction in synchrony with the conveyor, thereby maintaining the focus on the region as the item moves on the conveyor.

2. The inspection system of claim 1, wherein the first positioning mechanism is adapted and arranged to move the source in the first direction and the second positioning mechanism is adapted and arranged to the move the detector in the first direction.

3. The inspection system of claim 1, wherein the source collimator is shaped to pass a beam of radiation and the detector collimator is shaped to receive scattered radiation diffracted from the item on the conveyor at a scattering angle relative to the beam of radiation, and wherein the detector measures an energy spectrum of the scattered radiation diffracted at the scattering angle.

4. The inspection system of claim 3, wherein the controller is coupled to the detector collimator and adapted to vary the scattering angle of scattered radiation received at the detector.

5. The inspection system of claim 1, wherein the detector collimator comprises a movable stage carrying a plate having a plurality of apertures therein.

6. The inspection system of claim 5, wherein the plurality of apertures comprises a pinhole, a slit and an aperture having an x-ray fluorescent member disposed therein.

7. The inspection system of claim 1, wherein the x-ray source has an energy below about 120 keV.

8. The inspection system of claim 1, wherein the first positioning mechanism is constrained to position the source assembly in a first plane parallel to the first direction and the second positioning mechanism is constrained to position the detector assembly in a second plane parallel to the first plane.

9. A method of operating an inspection system having:
 a) an inspection region adapted and arranged to position an item under inspection in a plane;
 b) a source; and
 c) a detector;
 the method comprising:
  i. moving the source and the detector parallel to the plane in synchrony with the item to create a focus region in an item under inspection;
  ii. with the source, radiating a portion of the item under inspection, the portion including the focus region;

iii. with the detector, measuring radiation emanating at an angle from the focus region; and
iv. analyzing the measured radiation.

10. The method of claim 9, further comprising dithering the position of the source and detector while measuring radiation.

11. The method of claim 9, further comprising aligning the detector relative to the source by measuring with the detector radiation passing through a pinhole collimator.

12. The method of claim 9, wherein moving the source and the detector comprises positioning the source and detector with a separation in a first direction.

13. The method of claim 12, wherein measuring comprises measuring radiation passing through a detector collimator, the detector collimator comprising at least one aperture shaped as a slit, the slit having a narrow dimension in the first direction.

14. A method of operating an inspection system, the method comprising:
a) moving an item through an inspection area; and
b) gathering data on a focus region of the item using a source and a detector while moving the source and the detector synchronously with the item.

15. The method of claim 14, further comprising:
c) moving the source and detector other than synchronously with the item, whereby the source and detector are aligned with a second focus region of the item; and
d) subsequently gathering data on the second focus region of the item using the source and detector while moving the source and the detector synchronously with the item.

16. The method of claim 14, wherein moving an item comprises moving the item through the inspection area in a first direction and moving the source and detector other than synchronously with the item comprises moving the source and detector transverse to the first direction.

17. The method of claim 15, wherein moving the source and detector other than synchronously with the item comprises moving the source and detector different amounts.

18. The method of claim 14, wherein the inspection area is in a second inspection device and the method further comprises, prior to moving the item through the inspection area in the second inspection device, identifying the focus region in a first inspection device.

19. The method of claim 18, wherein the first inspection device and the second inspection device are coupled through a conveyor system and moving the item comprises moving the item on the conveyor system through the first inspection device and the second inspection device without stopping.

20. The method of claim 19, wherein the first inspection device inspects a series of items of which a plurality of items are identified for further inspection in the second device, items in the plurality are identified at a rate and the second inspection device inspects items at the same rate or higher.

21. The inspection system of claim 1, wherein the controller is further adapted to control the first and second positioning mechanisms to maintain a relative position of the item to the source assembly and the detector assembly.

22. The method of claim 9, wherein moving the source and the detector parallel to the plane in synchrony with the item further comprises maintaining a relative position of the item to the source and the detector.

23. The method of claim 14, wherein gathering data on a focus region of the item using a source and a detector while moving the source and the detector synchronously with the item further comprises maintaining a relative position of the item to the source and the detector.

* * * * *